United States Patent
Ward et al.

(10) Patent No.: US 7,329,506 B2
(45) Date of Patent: Feb. 12, 2008

(54) APPARATUSES AND METHODS FOR DETERMINING PROTEASE ACTIVITY

(75) Inventors: William W. Ward, Metuchen, NJ (US); Gavin C. Swiatek, Highland Park, NJ (US)

(73) Assignee: Rutgers, the State University, New Brunswick, NJ (US)

( * ) Notice: Subject to any disclaimer, the term of this patent is extended or adjusted under 35 U.S.C. 154(b) by 0 days.

(21) Appl. No.: 11/224,585

(22) Filed: Sep. 12, 2005

(65) Prior Publication Data

US 2006/0121552 A1   Jun. 8, 2006

Related U.S. Application Data

(60) Provisional application No. 60/632,931, filed on Dec. 3, 2004.

(51) Int. Cl.
*C12Q 1/37* (2006.01)
(52) U.S. Cl. .......................................... 435/23; 435/24
(58) Field of Classification Search .................. None
See application file for complete search history.

(56) References Cited

U.S. PATENT DOCUMENTS

| 6,680,178 B2 | 1/2004 | Harris et al. .................. 435/23 |
| 2004/0014134 A1 | 1/2004 | Kuhlemann et al. ......... 435/7.1 |
| 2004/0265902 A1 | 12/2004 | Fricker et al. ............... 435/7.1 |
| 2005/0214890 A1* | 9/2005 | Tan et al. ..................... 435/23 |

FOREIGN PATENT DOCUMENTS

WO    WO 0212543 A2 *  2/2002

* cited by examiner

*Primary Examiner*—Jon Weber
*Assistant Examiner*—Paul Martin
(74) *Attorney, Agent, or Firm*—Licata & Tyrrell PC

(57) ABSTRACT

The present invention relates to compositions and an apparatuses for determining protease activity. The compositions of the invention contain a reporter protein fused to at least one protease cleavage sequence, and a linker for attaching the protease cleavage sequence to a solid support. Methods for determining protease activity and characterizing proteases are also provided.

2 Claims, No Drawings

APPARATUSES AND METHODS FOR DETERMINING PROTEASE ACTIVITY

INTRODUCTION

This application claims the benefit of priority from U.S. provisional patent application Ser. No. 60/632,931, filed Dec. 3, 2004, the content of which is incorporated herein by reference in its entirety.

BACKGROUND OF THE INVENTION

Cells, tissues, organs, organisms and extracts thereof contain a variety of known and yet to be characterized proteases. Many of these proteases interfere with the expression, extraction and purification of desired proteins from natural sources or from recombinant organisms. Custom production of proteins for pharmaceutical research or medical applications can be compromised by the presence of proteases in extracts. Elimination of proteolysis during protein purification is difficult and further complicated by a lack of knowledge about the proteases present and the nature of the protease specifically cleaving the protein being purified.

Assays for detecting protease activity are known in the art. For example, fluorescence resonance energy transfer (FRET)-based methods are disclosed in U.S. patent application Ser. Nos. 10/477,044 and 10/343,977. These assays employ two fluorescent proteins attached via a protease cleavage linker, wherein cleavage of the linker results in a reduction in the level of FRET.

Moreover, U.S. Pat. No. 6,680,178 discloses a fluorogenic moiety, such as 7-amino-4-carbamoylmethyl-coumarin, covalently bound to a peptide sequence for identifying the primary and extended specificity of enzymes such as proteases.

Needed in the art is a rapid, cost-effective assay that can be used to quantitate protease activity, as well as be used to identify the type of protease being assayed. The present invention meets this long-felt need.

SUMMARY OF THE INVENTION

The present invention is a composition for determining protease activity. The composition is composed of a reporter protein fused to at least one protease cleavage sequence, and a linker for attaching the protease cleavage sequence to a solid support. One embodiment encompasses a test apparatus composed of at least one composition of the invention and a solid support. Another embodiment embraces an array of compositions and a solid support.

In a further embodiment, an apparatus of the invention is used in a method for determining protease activity. The method involves contacting a protease with said apparatus and using the reporter protein to determine activity.

In yet a further embodiment, an apparatus of the invention is used in a method for characterizing a protease. The method involves contacting a protease with said apparatus to produce a profile and evaluating the profile for selected characteristics thereby characterizing the protease.

An isolated nucleic acid encoding the composition of the invention, as well as a vector and host cell are also provided.

DETAILED DESCRIPTION OF THE INVENTION

The present invention relates to cost-effective compositions and assays for detecting and quantitating protease activity, as well as characterizing proteases. A composition of the instant invention is composed of a reporter protein fused to at least one protease cleavage sequence, and a linker which attaches the protease cleavage sequence to a solid support. In particular embodiments of the instant invention, all three components (i.e., the reporter protein, protease cleavage sequence, and linker) are proteinaceous and translated from a recombinant monocistronic mRNA to generate a chimeric or hybrid protein. Assays employing the composition of the invention are carried out by contacting the protein composition with a protease and measuring the presence and/or amount of reporter protein released from, or remaining attached to, the solid support. In such assays, the strength of the signal generated by the reporter protein is proportional to the activity of the protease. For example, a protease, which specifically recognizes a particular protease cleavage sequence, will readily cleave the composition of the invention and release high levels of reporter protein. In contrast, a protease, which has a reduced specificity or does not recognize a particular protease cleavage sequence will, release low levels of reporter protein or no reporter protein, respectively, from the solid support. Accordingly, the instant assays are useful for detecting the presence, the level of activity, and substrate specificity of a protease. Further, when a plurality of different protease cleavage sequences is employed in an array, the identity of an unknown protease can be ascertained. Moreover, the instant assays can be used to identify protease inhibitors with a high degree of specificity to a particular protease or family of proteases.

A reporter protein, as used in the context of the instant invention, is a protein that is readily detectable either by its presence, or by its activity, which results in the generation of a detectable signal. Reporter proteins which are detected based upon their activity, include, but are not limited to, reporter enzymes such as β-galactosidase (Nolan, et al. (1988) *Proc. Natl. Acad. Sci. USA* 85:2603-2607), chloramphenicol acetyltransferase (CAT; Gorman, et al. (1982) *Mol. Cell Biol.* 2:1044; Prost, et al. (1986) *Gene* 45:107-111), β-lactamase, β-glucuronidase and alkaline phosphatase (Berger, et al. (1988) *Gene* 66:1-10; Cullen, et al. (1992) *Methods Enzymol.* 216:362-368). The presence and amount of reporter enzyme present can be measured via its enzymatic action on a substrate resulting in the formation of a detectable reaction product. The methods of the invention provide means for measuring the amount of reaction product, wherein the amount of reaction product generated or the remaining amount of substrate is related to the amount of reporter enzyme activity. For some enzymes, such as β-galactosidase, β-glucuronidase and β-lactamase, well-known fluorogenic substrates are available that allow the enzyme to covert such substrates into detectable fluorescent products.

A variety of bioluminescent, chemiluminescent and autofluorescent proteins, referred to herein as light-emitting reporter proteins, are also useful in the instant assay. Exemplary light-emitting reporter proteins, which require a cofactor to emit light include, but are not limited to, the luciferase protein from firefly, *Photinus pyralis* (De Wet, et al. (1987) *Mol. Cell. Biol.* 7:725-737); the yellow fluorescent protein from *Vibrio fischeri* strain Y-1 which requires flavins as fluorescent co-factors (Baldwin, et al. (1990) *Biochemistry* 29:5509-15); the Peridinin-chlorophyll a binding protein from the dinoflagellate *Symbiodinium* sp. (Morris, et al. (1994) *Plant Mol. Biol.* 24:673:77); and the phycobiliproteins from marine cyanobacteria such as *Synechococcus*, e.g., phycoerythrin and phycocyanin (Wilbanks, et al. (1993) *J. Biol. Chem.* 268:1226-35).

For convenience and efficiency, particular embodiments of the instant invention encompass the use of a light-emitting reporter protein that is an autofluorescent reporter protein. As used herein, an autofluorescent reporter protein is any protein capable of fluorescence when excited with appropriate electromagnetic radiation and does not require a cofactor or substrate to emit light. This includes fluorescent proteins whose amino acid sequences are either natural or engineered. Suitable autofluorescent reporter proteins for use in the instant invention include those from the green fluorescent protein (GFP) family of polypeptides, which are derived from the jellyfish species Aequoria victoria. A variety of useful Aequorea-related GFPs have been engineered by modifying the amino acid sequence of the naturally occurring GFP to create GFP mutants (Prasher, et al. (1992) Gene 111:229-233;Heim, et al. (1994) Proc. Natl. Acad. Sci. USA 91:12501-04; U.S. Pat. No. 5,625,048; PCT/US95/14692). Several basic classes of useful GFP mutants include red-shifted GFP, which has an emission peak around 511 nm but lacks the near-UV 395 nm excitation peak; blue fluorescent protein (BFP); cyan fluorescent protein (CFP); sapphire; and yellow fluorescent protein (YFP). See, e.g., Pollok and Heim (1999) Trends Cell Biol. 9:57-60. Another suitable GFP variant is a pH-insensitive YFP protein having Val68Leu and Gln69Lys mutations (Miyawaki, et al. (1999) Proc. Natl. Acad. Sci. USA 96:2135-2140). While wild-type GFP is suitable for use above pH 6.0, this YFP protein could be useful under acidic assay conditions. Fluorescent proteins from the sea pansy, Renilla reniformis, and Phialidium gregarium are also contemplated. See, Ward, et al. (1982) Photochem. Photobiol. 35:803-808; Levine, et al. (1982) Comp. Biochem. Physiol. 72B:77-85. The coding sequences for these autofluorescent reporter proteins are well-known in the art and can be used to recombinantly produce the protein composition disclosed herein.

In particular embodiments of the instant invention, the reporter protein does not bind to or interact, either covalently or non-covalently, with the solid support. In other embodiments, the reporter protein is monomeric and is protease resistant. Protease resistance can be determined by exposing an isolated reporter protein of interest to one or more proteases and determining whether the reporter protein produces an equivalent amount of activity in the presence and absence of the protease. Alternatively, protease resistance can be assessed by SDS-PAGE analysis.

Full-length recombinant GFP is 238 amino acids long; however, crystal structure analysis of GFP only shows the N-terminal 230 amino acid residues because the eight C-terminal amino acid residues represent a flexible region of the protein which cannot be seen by X-ray crystallography. Without amino acid substitutions in this C-terminal region, the C-terminal tail is susceptible to proteolytic cleavage by a variety of proteases. As exemplified herein, removing the C-terminal 6-10 amino acid residues of wild-type Aequoria victoria GFP and replacing these amino acids with a protease cleavage sequence had no effect on GFP autofluorescence. An exemplary GFP lacking the C-terminal amino acid residues is presented herein as SEQ ID NO:1. Thus, one embodiment of the instant invention is a GFP protein lacking the C-terminal 6, 8, or 10 amino acid residues. In another embodiment, the autofluorescent reporter protein has an amino acid sequence of SEQ ID NO:1 or shares, over the entire length of the protein sequence, at least 85%, 90%, 95%, 97% or 99% amino acid sequence identity with an amino acid sequence of SEQ ID NO:1.

As used in the context of the instant invention, a protease cleavage sequence is an oligopeptide (e.g., 10 to 30 amino acid residues) substrate which is recognized and cleaved by a particular protease or family of proteases. In accordance with the instant invention, at least one protease cleavage sequence is fused or operably linked to the reporter protein. As used herein, fused or operably linked is intended to mean that the reporter protein and protease cleavage sequence are joined by peptide bonds to create a contiguous protein sequence. To increase the effective concentration of a protease cleavage sequence in the protease assays of the instant invention, particular embodiments encompass the use of at least two, three, four, five, six, seven, eight or more protease cleavage sequences fused, in tandem, to a reporter protein.

In some embodiments, the protease cleavage sequence is fused to the C-terminus of the reporter protein. In other embodiments, the protease cleavage sequence is fused to the N-terminus of the reporter protein. When the reporter protein is a GFP and the protease cleavage sequence is fused to the N-terminus, GFP can contain or lack the C-terminal 6 to 10 amino acid residues. When the reporter protein is a GFP and the protease cleavage sequence is fused to the C-terminus, GFP desirably lacks the C-terminal 6 to 10 amino acid residues so that release of GFP from the solid support is via cleavage of the protease cleavage sequence and not cleavage of the GFP sequence.

Exemplary protease cleavage sequences which can be used to detect protease activity in accordance with the instant assays include, but are not limited to, the protease cleavage sequences listed in Table 1.

TABLE 1

| Protease | Protease Cleavage Sequence | SEQ ID NO: |
| --- | --- | --- |
| HIV-1 protease | VSQYVIV | 2 |
| Tobacco etch virus protease | ENLYFQG | 3 |
| Prohormone convertase | PSPREGKRSY | 4 |
| Interleukin-1β-converting enzyme | YVADG | 5 |
| Adenovirus endopeptidase | MFGGAKKR | 6 |
| Cytomegalovirus protease | RGVVNASSRLA | 7 |
| Leishmanolysin | LIAYLKKAT | 8 |
| Amyloid precursor protein β-Secretase | VKMDAEF | 9 |

TABLE 1-continued

| Protease | Protease Cleavage Sequence | SEQ ID NO: |
| --- | --- | --- |
| Thrombin | LVPRGS | 10 |
| Renin/angiotensin converting enzyme | DRVYIHPFHLVIH | 11 |
| Cathepsin D | KPALFFRL | 12 |
| Kininogenases | QPLGQTSLMKRPPGFSPFR | 13 |
| Herpes simplex virus protease | LVLASSSF | 14 |
| Sering protease plasmin | KXYK | 15 |
| Factor $X_a$ | IEGR | 16 |

Other suitable protease cleavage sequences are known in the art and a comprehensive list of proteases and their cognate cleavage sequences is available from the MEROPS database located on the world-wide web (see Rawlings, et al. (2002) *Nucl. Acids Res.* 30:343-346).

It is contemplated that the protease cleavage sequence can be natural, engineered, or alternatively, obtained from a random peptide library, i.e., a combination of two or more amino acid residues constructed so that the complete sequence of a particular oligopeptide is not preselected. Engineered or random oligopeptides can be used in assays to delineate the range of sequences which can be cleaved by a particular protease.

To the protease cleavage sequence is conjugated, or operably linked, a linker for attaching the protease cleavage sequence to a solid support. As used in the context of the instant invention, a linker is a chemically reactive moiety which, in some embodiments, covalently binds to a solid support. In other embodiments, the linker provides a strong non-covalent bond to the solid support (e.g., an antibody-antigen interaction). Independent of whether the bond is covalent or non-covalent, the linker employed should have a minimal amount of leaching (i.e., slow release) from the solid support. Suitable linkers are desirably protease resistant and include, but are not limited to, affinity tags (e.g., a maltose binding domain, biotin, FLAG®, etc.), carbohydrates (e.g., post-translationally incorporated or conjugated to the protein composition), Fc fragments of an antibody, or chemically reactive amino acids. In particular embodiments, the linker is one or more chemically reactive amino acids such as a cysteine, a cys-gly-cys or a polyhistidine. Desirably, proteinaceous linkers are operably linked to the protease cleavage sequence by a peptide bond (e.g., via recombinant expression). Alternatively, proteinaceous and non-proteinaceous linkers can be chemically conjugated to the protease cleavage sequence using convention Fmoc or Tboc chemistries. The linker can be conjugated or operably linked to the protease cleavage sequence at the C- or N-terminus depending upon the attachment of the protease cleavage sequence to the reporter protein. For example, orientations can include: $NH_2$-reporter protein->protease cleavage sequence->linker-COOH or $NH_2$-linker->protease cleavage sequence->reporter protein-COOH. Exemplary compositions of the former orientation are presented herein as SEQ ID NO:17, SEQ ID NO:18, SEQ ID NO:19, SEQ ID NO:20. Each of these exemplary compositions contain GFP followed by a non-specific or specific protease cleavage sequence and linker. SEQ ID NO:17 has one copy of the protease cleavage sequence SVPSGCG (SEQ ID NO:21) and a five histidine residue linker; SEQ ID NO:18 has three tandem copies of the tobacco etch virus protease cleavage sequence ENLYFQG (SEQ ID NO:3) and a C-terminal cysteine residue; SEQ ID NO:19 has two tandem copies of the Factor $X_a$ protease cleavage sequence IEGR (SEQ ID NO:16) and a C-terminal cysteine residue; and SEQ ID NO:20 has three tandem copies of the thrombin protease cleavage sequence LVPRGS (SEQ ID NO:10) and a C-terminal cysteine residue.

It is contemplated that the reporter protein, protease cleavage sequence and linker can be immediately adjacent to one another or can be attached via short, e.g., 1-10, amino acid residue, protease-resistant spacers. The spacer can be, e.g., an amino acid such as alanine, valine, isoleucine, or a poly-glycine moiety. Other spacers are known in the art. For example, to improve site-specific cleavage of a methionyl porcine growth hormone [[Met$^1$]-pGH(1-46)-IGF-II] fusion protein by the enzyme H64A subtilisin, a series of flexible, unstructured spacer peptides N-terminal to the cleavage sequence can be introduced (Polyak (1997) *Protein Eng.* 10:615-619).

Covalent attachment of the linker to the solid support is dependent upon the linker employed. For example, when the linker contains a sulfhydryl group (e.g., a cysteine amino acid residue), a maleimide-coated solid support can be used to immobilize the composition of the instant assay. Similarly, a hydrazine surface can be used to covalently couple a periodate-activated carbohydrate or glycosylated protein (e.g., Fc fragments of an antibody) to a solid support. Further, attachment of polyhistidine residues to metal affinity supports is well-established in the art. Other suitable chemistries for covalently attaching biomolecules to solid supports are well-known in the art and can be employed herein. Strong, non-covalent attachments can be achieved using, e.g., an affinity tag such as an antigen which binds a cognate antibody or Fab fragment immobilized on the solid support.

Solid supports come in a variety of forms including, but not limited to, membrane filters (e.g., cellulose discs), beads (including latex, glass, paramagnetic particles, pre-activated affinity, etc.), glass slides and silicon wafers (e.g., used in chip-based microarray analysis), multi-well plates, and the like. Selection of the solid support can be dependent upon the protease being assayed and compatibility of instrumentation and robotic systems. Microarray slides or wafers, or polystyrene multi-well plates (e.g., 96-, 384-, and 1536-well) are particularly suitable because pipetting, washing and signal detection are easily automated for precision analysis. Other advantages include the ability to analyze multiple samples simultaneously and compatibility with a number of different detection systems (e.g., calorimetric, fluorescent and chemiluminescent). Moreover, transferable solid phase devices, e.g., lids with 96 projections, prongs or pins corresponding to the wells of a 96-well plate are commercially available (e.g., NUNC-IMMUNO™ TSP available with POLYSORP™ or MAXISORP™ surfaces). The pins of such a 96-well plate lid can be coated with the composition of the invention and a plurality of protease reactions can be simultaneously carried out. Moreover, multiple lids, containing a plurality of protease cleavage sequences can be submerged into samples held in a single 96-well plate.

Accordingly, one embodiment of the instant invention encompasses a protease activity test apparatus composed of a solid support with at least one composition of the invention (i.e., the reporter protein, protease cleavage sequence, and linker) attached thereto. As will be appreciated by one of skill in the art, a variety of protease cleavage sequences and reporter protein combinations can be envisioned thereby generating arrays of compositions. Thus, particular embodiments of the instant invention encompass a test apparatus composed of a solid support with at least 2, 3, 4, 5, 6, 7, 8, 10, 12, 16, 24, 32, 48, 96, 384, 1536, or more different compositions arrayed thereon. Moreover, a plurality of concentrations of each composition can be employed. By way of illustration, the 12 vertical columns of a 96-well plate or lid thereof can be coated with a different composition (e.g., 12 different protease cleavage sequences, each with the same reporter protein and linker) replicated in 8 horizontal rows, wherein each well of the 8 horizontal rows has a different concentration of composition (e.g., row 1 is diluted 1-fold; row 2 is diluted 2-fold, row 3 is diluted 5-fold, etc). Alternatively, each column and row can be coated with a composition containing a different protease cleavage sequence (i.e., 96 different compositions). It is contemplated that an apparatus can have a protease cleavage sequence specific for each family of protease (i.e., serine proteases, cysteine proteases, aspartic proteases, and metalloproteases), a protease cleavage sequence for individual members of a family (e.g., a substrate specific for caspase 1 to 14), or can be custom designed based upon the needs of a user.

Compositions of the instant invention can be produced by recombinant DNA technology or chemically synthesized, or produced by a combination thereof. A protein composition produced by recombinant DNA technology is generally expressed from a nucleic acid encoding the protein. Such a nucleic acid can be isolated by conventional methodologies such as restriction enzyme-based cloning. For example, DNA fragments coding for the different protein or peptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, the isolated nucleic acid molecule can be synthesized by conventional techniques including automated DNA synthesis or polymerase chain reaction (PCR) amplification. PCR amplification of gene fragments can be carried out using anchor primers which give rise to complementary overhangs between two consecutive gene fragments which are subsequently annealed and reamplified to generate a chimeric gene sequence (see, e.g., Current Protocols in Molecular Biology, eds. Ausubel, et al. John Wiley & Sons, 1992). When protease cleavage sequences and proteinaceous linkers are short peptides, nucleic acids encoding these peptides can be incorporated into the 5' or 3' anchor primers used to amplify the reporter protein. (i.e., add-on PCR) As used herein, an isolated nucleic acid is intended to mean a nucleic acid molecule separated or substantially free from other nucleic acids commonly found associated with the molecule. Exemplary isolated nucleic acids encoding protein compositions of the instant invention, i.e., SEQ ID NO:17-20, are respectively set forth herein as SEQ ID NO:22, SEQ ID NO:23, SEQ ID NO:24 and SEQ ID NO:25.

To generate mutant versions of the reporter protein, site-specific mutagenesis or random mutagenesis can be employed, e.g., by increasing the error rate of PCR of the original polynucleotide with 0.1 mM $MnCl_2$ and unbalanced nucleotide concentrations. See, e.g., U.S. patent application Ser. No. 08/337,915; U.S. Pat. No. 5,625,048 or PCT/US95/14692.

Recombinant production of a desired protein typically involves directly expressing the desired protein from a recombinant expression vector or expressing the desired protein with a heterologous protein sequence such as a tag or a signal sequence to facilitate purification or secretion of the desired protein from a host cell. In certain host cells (e.g., mammalian host cells), expression and/or secretion of a desired protein can be increased through use of a heterologous signal sequence.

A recombinant expression vector generally harbors nucleic acids encoding the desired protein in a form suitable for expression, i.e., the recombinant expression vector includes one or more regulatory sequences operatively-linked to the nucleic acid to be expressed. Expression vector and recombinant expression vector are used interchangeably herein, and in the context of a recombinant expression vector, operatively-linked is intended to mean that the nucleic acid of interest is linked to the regulatory sequence(s) in a manner which allows for expression of the nucleic acid (e.g., in an in vitro transcription/translation system or in a host cell). A regulatory sequence is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleic acid in many types of host cells and those which direct expression of the nucleic acid only in certain host cells (e.g., tissue-specific regulatory sequences). It will be appreciated by one of skill in the art that the design of the expression vector depends on such factors as the choice of the host cell to be transformed, the level of expression of the desired protein, and the like.

A recombinant expression vector can be designed for expression of a desired protein in prokaryotic or eukaryotic cells. For example, a protein composition of the instant invention can be expressed in bacterial cells such as *E. coli*, insect cells (using baculovirus expression vectors), yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Examples of suitable inducible *E. coli* expression vectors include pTrc (Amann, et al. (1988) *Gene* 69:301-315) and pET 1d (Studier, et al. (1990) *Meth-* ods *Enzymol.* 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

A yeast expression vector also encompassed within the scope of the invention. Examples of vectors for expression in yeast such as *Saccharomyces cerevisiae* include pYepSec 1 (Baldari, et al. (1987) *EMBO J.* 6:229-234), pMFa (Kurjan and Herskowitz (1982) *Cell* 30:933-943), pJRY88 (Schultz, et al. (1987) *Gene* 54:113-123), pYES2 (INVITROGEN™ Corp., San Diego, Calif.), and picZ (INVITROGEN™ Corp., San Diego, Calif.).

Alternatively, a protein composition of the invention can be expressed in insect cells using baculovirus expression vectors. Baculovirus vectors available for expression of proteins in cultured insect cells (e.g., Sf9 cells) include the pAc series (Smith, et al. (1983) *Mol. Cell Biol.* 3:2156-2165) and the pVL series (Lucklow and Summers (1989) *Virology* 170:31-39) of vectors.

Further, nucleic acids encoding the instant protein composition can be expressed in mammalian cells using a mammalian expression vector. Examples of mammalian expression vectors include any one of the well-known recombinant viral vectors including pCDM8 (Seed (1987) Nature 329:840) and pMT2PC (Kaufman, et al. (1987) *EMBO J.* 6:187-195). When used in mammalian cells, the control functions of the expression vector are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, et al. (1989) Molecular Cloning: A Laboratory Manual. $2^{nd}$ ed., Cold Spring Harbor Laboratory, Cold Spring Harbor Laboratory Press, Cold Spring Harbor, N.Y.

A recombinant mammalian expression vector can also be used to direct expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al. (1987) *Genes Dev.* 1:268-277), pancreas-specific promoters (Edlund, et al. (1985) *Science* 230:912-916), and mammary gland-specific promoters (e.g., milk whey promoter; U.S. Pat. No. 4,873,316 and EP 264,166).

Recombinant expression vectors in which the nucleic acid of interest is homologously recombined into a specific site of the host cell's genome are also contemplated. The terms host cell and recombinant host cell are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell encompassed within the scope of the instant invention is any prokaryotic or eukaryotic cell. In particular embodiments, the protease does not produce or produces reduced levels of endogenous protease to facilitate purification of an intact protein composition. For example, a protein composition of the invention can be expressed in bacterial cells such as protease-deficient *E. coli*.

A mammalian host cell can also be used to produce non-human transgenic animals. For example, a host cell can be a fertilized oocyte or an embryonic stem cell into which recombinant expression vector has been introduced. Such host cells can then be used to create non-human transgenic animals according to well-established methods. Exemplary examples of non-human animals include, but are not limited to, mice, goats, sheep, pigs, cows or other domestic farm animals. Such transgenic animals are useful, for example, for large-scale production of the protein composition of the invention (gene pharming).

Expression vector DNA can be introduced into prokaryotic or eukaryotic cells via conventional transformation or transfection techniques. As used herein, the terms transformation and transfection are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (1989) supra, and other laboratory manuals.

To identify and select transformed or transfected host cells, a gene that encodes a selectable marker (e.g., resistance to antibiotics) is generally introduced into the host cells along with the nucleic acid of interest. Suitable selectable markers include those which confer resistance to drugs, such as G418, hygromycin and methotrexate. Nucleic acids encoding a selectable marker can be introduced into a host cell on the same vector as that encoding the protein of interest or can be introduced on a separate vector. Cells stably transformed or transfected with the introduced nucleic acid can be identified by drug selection (e.g., cells that have incorporated the selectable marker gene will survive, while the other cells die).

Once produced, the desired protein is either recovered as a secreted protein or from host cell lysates, when directly expressed without a secretory signal. Purification of the protein composition from recombinant cell proteins can be carried out by centrifuging the culture medium or lysate to remove particulate cell debris and purifying the protein composition by, e.g., fractionation on immunoaffinity or ion-exchange columns, ethanol precipitation, chitin column chromatography, reverse phase HPLC, chromatography on silica or on a anion-exchange resin such as DEAE, chromatofocusing, SDS-PAGE, ammonium sulfate precipitation, gel filtration, or ligand affinity chromatography (e.g., $Ni^{2+}$-agarose chromatography).

In addition to recombinant production, the protein composition can be produced by direct peptide synthesis using solid-phase techniques (Merrifield (1963) *J. Am. Chem. Soc.* 85:2149-2154). Protein synthesis can be performed using manual techniques or by automation. Automated synthesis can be achieved, for example, using Applied Biosystems 431A Peptide Synthesizer (Perkin Elmer, Boston, Mass.). Various fragments of the protein composition can be chemically-synthesized separately and combined using chemical methods to produce the full-length molecule. A number of cross-linkers are well-known in the art, including homo- or hetero-bifunctional cross-linkers, such as BMH, SPDP, etc. Chemical methods for cross-linking molecules to the amino- or carboxy-terminus of a protein are reviewed by Offord (1992) In: Protein Engineering—A Practical Approach, Rees, et al., eds., Oxford University Press.

Whether recombinantly-produced or chemically-synthesized, the protein composition of the invention can be further modified before use in the assays disclosed herein. For example, the protein composition can be glycosylated or phosphorylated using well-known methods.

The compositions and test apparatuses of the instant invention are particularly suitable for determining protease activity and characterizing known and unknown proteases. These assays take advantage of the fact that cleavage of the protease cleavage sequence releases the reporter protein from the solid support such that the released reporter protein or reporter protein remaining bound to the solid support can be detected.

One embodiment of the invention encompasses a method for determining protease activity by contacting a protease with a test apparatus of the invention and using the reporter protein to determine activity of the protease. Using the reporter protein to determine protease activity is intended to mean that by virtue of the proportional relationship that exists between protease activity and reporter protein released, the presence or amount of reporter protein released from, or remaining bound to, the solid support is indicative of the presence or amount of activity of the protease. To illustrate, a pin or prong with the reporter protein attached thereto is submerged into a well containing a test sample containing or suspected of containing a protease, after a specified amount of time (e.g., 10 minutes to 24 hours) the pin or prong is removed from the well and the presence or amount of the released reporter protein in the well is detected. In this illustrative example, the amount of reporter protein released is directly proportional to the activity of the protease. In an alternative assay, the reporter protein is attached to a membrane (e.g., located in the base of a column or well) or glass slide, the test sample is applied to the surface of the membrane for a specified amount of time, the reporter protein released into the test sample is removed (e.g., by a vacuum or washing), and the reporter protein remaining bound to the membrane or slide is detected. In this case, the amount of protease activity is inversely proportional to the amount of reporter protein remaining bound to the solid support. As will be appreciated by the skilled artisan, methods and devices for detecting reporter enzyme and bioluminescent, chemiluminescent and autofluorescent reporter protein activity are well-known and routinely used in the art. For example, assays with fluorescent materials are disclosed in, e.g., Lackowicz, J. R., 1983, *Principles of Fluorescence Spectroscopy*, New York:Plenum Press.

Because of the sensitivity (i.e., signal-to-noise ratios in the range of 1000:1 to 10,000:1) and adaptability of the instant assay, the test apparatus can contain arrays of protease cleavage sequences for characterizing a protease. Accordingly, another embodiment of the instant invention encompasses a method for characterizing a protease by contacting a protease with an array of compositions of the invention to produce a profile and evaluating the profile for selected characteristics. For example, the array of compositions can be 12 different protease cleavage sequences, at 8 different concentrations, arrayed in a 96-well plate or lid thereof. The ability of a test protease to cleave one or more of the 12 different protease cleavage sequences as well as the amount of activity toward a particular protease cleavage sequence is used to generate a profile or pattern of characteristics for the test protease. It is contemplated that a profile can also include sensitivity to one or more protease inhibitors. Once the profile is generated, it is evaluated either manually or via a computer for selected characteristics such as substrate specificity, inhibitor specificity, etc. The selected characteristics of a particular test protease are indicative of the type of protease or protease family. It is contemplated that a database of profiles (e.g., with ratiometric numbers or histograms) for a plurality of known proteases can be generated and, via computer-assisted pattern recognition algorithms, used for comparing profiles of test or unknown proteases, thereby characterizing and identifying the test or unknown protease. The database of profiles can be provided to a user (e.g., on disk, CD or accessible via the internet) in conjunction with a test apparatus so that characterization of a test protease can be readily conducted. Alternatively, a collection of pure, known proteases (i.e., control samples) can be assayed simultaneously with the test protease and a direct comparison can be conducted to characterize the protease.

Proteases that can be detected and characterized by the instant assays are those generally classified as serine proteases, cysteine proteases, aspartic proteases, and metalloproteases.

The serine proteases encompass two distinct families, the chymotrypsin family which includes the mammalian enzymes such as chymotrypsin, trypsin or elastase or kallikrein; and the substilisin family which include bacterial enzymes such as subtilisin. The general three-dimensional structure is different in the two families but they have the same active site geometry. The serine proteases exhibit different substrate specificities, which are related to amino acid substitutions in the various enzyme subsites (see, Schechter & Berger (1967) *Biochem. Biophys. Res. Com.* 27:157-162) interacting with the substrate residues. Some enzymes have an extended interaction site with the substrate, whereas others have a specificity restricted to the P1 substrate residue. Three residues which form the catalytic triad are essential in the catalytic process, i.e., His-57, Asp-102 and Ser-195 (based upon location in chymotrypsinogen).

The cysteine proteases include plant proteases such as papain, actinidin or bromelain, several mammalian lysosomal cathepsins, the cytosolic calpains (calcium-activated), as well as several parasitic proteases (e.g., *Trypanosoma, Schistosoma*) and the apoptosis-related caspases. Papain is the archetype member of the family. Like the serine proteases, catalysis proceeds through the formation of a covalent intermediate and involves a cysteine and a histidine residue. The essential Cys-25 and His-159 (based upon location in papain) play the same role as Ser-195 and His-57, respectively.

Most of the aspartic proteases belong to the pepsin family. The pepsin family includes digestive enzymes such as pepsin and chymosin as well as lysosomal cathepsins D and processing enzymes such as renin, and certain fungal proteases (e.g., penicillopepsin, rhizopuspepsin, endothiapepsin). A second family encompasses viral proteases such as the protease from the AIDS virus (HIV) also called retropepsin.

The metalloproteases differ widely in their sequences and their structures but the great majority of enzymes contain a zinc atom which is catalytically active. In some cases, zinc is replaced by another metal such as cobalt or nickel without loss of the activity. Bacterial thermolysin has been well-characterized and its crystallographic structure indicates that zinc is bound by two histidines and one glutamic acid. Enzymes of this family include thermolysin, neprilysin, alanyl aminopeptidase, and astacin.

The assays of the invention can be used in drug screening assays to identify compounds that alter the activity of a protease. For example, a sample containing a known amount of protease is contacted with a test apparatus of the invention and with a test compound. The amount of the protease activity in the sample is then determined as above, e.g., by determining the release of reporter protein after contact between the sample, the test apparatus and the compound. Then the amount of activity per mole of protease in the presence of the test compound is compared with the activity per mole of protease in the absence of the test compound. A difference indicates that the test compound alters the activity of the protease.

The instant assays can also be used to determine the activity of a genetically altered protease, the presence and type of protease contaminant in a large-scale protein preparation, and the kinetic constant of a protease. Further, a mixture of unknown proteases could be evaluated to identify the individual components based upon activity toward particular protease cleavage sequences. As such, a tailored cocktail of inhibitors can be employed to target specific proteases. Moreover, the purity of a protease or substrate preparation (e.g., quality control during manufacture) can be readily ascertained. For example, collagenase has multiple isoforms, each with slightly different substrate specificities. Purification of the various isoforms to homogeneity is difficult. It is contemplated that with the instant assay, a 1% difference in substrate specificity could be detected and quantified to monitor purity of collagenase isoform preparations. Further, the quality of a sequence-grade protease preparation can be determined as can the effectuality of a protease inhibitor.

Advantages of the instant apparatuses and methods include the ease and low cost of producing large quantities of customized substrates, particularly when the reporter protein, protease cleavage sequence and linker are proteinaceous and translated as one contiguous protein; high levels of recovery (~50%) from crude extract to final pure product; and the use of one type of chemistry to attach the linker to the solid support (e.g., sulfhydryl chemistry to attach a C- or N-terminal cysteine).

The invention is described in greater detail by the following non-limiting examples.

EXAMPLE 1

Polyhistidine Linker

A hybrid GFP construct containing a protease cleavage sequence was produced by PCR amplification. GFP was selected because certain reactive amino acid groups are not exposed on the surface of the protein, lending a high degree of chemical specificity for binding of the linker to the solid support (i.e., no region of GFP interacts with or binds to the solid support). For example, the two cysteine residues of GFP are buried within the beta-barrel and were found to be inaccessible to chemical modifying agents, as determined by no detectable reaction with DTNB and by molecular graphic accessibility calculations.

The 3' primer for PCR amplifying GFP not only contained sequences for hybridization to the 3' portion of the GFP coding sequence, but also contained coding sequence for the protease cleavage sequence SVPSGCG (SEQ ID NO:21) followed by six histidine residues. The resulting hybrid protein is presented herein as SEQ ID NO:17. The hybrid GFP construct was expressed in a protease-minus *E. coli* strain and purified using DTNB agarose chromatography. GFP was bound to immobilized metal affinity chromatography (IMAC) beads with chelated nickel ions via the six histidine residues. The hybrid GFP construct bound tightly to the beads and after extensive washing, no further leaching was detected. The washed beads were portioned out equally among 15 microfuge tubes. As positive controls, two of the tubes were subjected to treatment with EDTA (a metal chelator that strips the nickel ions from the beads, thus releasing GFP almost quantitatively). Three tubes were untreated (i.e., negative controls). The remaining 10 tubes were exposed to small amounts of different proteases. All tubes were left overnight with vigorous shaking. The contents of each tube were emptied into separate nine-inch, glass bead-plugged Pasteur pipettes and the trapped beads were washed with buffer to elute released GFP into collection tubes placed below the columns. The amount of GFP released was measured with a fluorometer.

By visual inspection, EDTA released virtually all the GFP in the positive controls, whereas no GFP leached from the three negative controls. Results from the assays carried out in the presence of the proteases are presented in Table 2.

TABLE 2

| Protease | Micrograms of GFP Released by Protease |
| --- | --- |
| Papain | 244 |
| Purified Bromelain | 35 |
| Crude Bromelain | 86 |
| Trypsin (Sample 1) | 9 |
| Trypsin (Sample 2) | 56 |
| Pancreatin | 137 |
| Proteinase K | 94 |
| Chymotrypsin | 47 |
| Elastase | 94 |
| Pepsin | 0* |
| EDTA (Control 1) | 236 |
| EDTA (Control 2) | 214 |
| Untreated (#1) | 0 |
| Untreated (#2) | 0 |
| Untreated (#3) | 0 |

*Assay was carried out pH 8.0 and pepsin is active under acid conditions.

The most effective enzyme was elastase, with positive results apparent within five minutes after adding the enzyme. However, papain, pancreatin, and proteinase K released as much or more GFP in the overnight incubation. As elastase digests collagen which is rich in proline and glycine, and the protease cleavage sequence used resembled collagen in its amino acid composition, cleavage of this protease cleavage sequence by elastase was expected. Samples with no detectable GFP are significant, as these samples were measured without dilution on a very sensitive fluorometer. In contrast, samples with detectable amounts of GFP required a 10X dilution to be on scale.

EXAMPLE 2

Effects of EDTA

As a His-tagged GFP can be released from nickel IMAC beads in the presence of EDTA, experiments presented in Example 1 were repeated in the presence of $Ca^{2+}$ to sequester any EDTA present in the protease salts and eliminate unwanted release of GFP by metal chelation. Bromelain was isolated to 98% homogeneity (as determined by size exclusion HPLC in the absence of metal chelators such as EDTA, $NH_3$, and citrate). All proteases were dissolved in 10 mM $CaCl_2$ in 10 mM Tris buffer at pH 8.0. Bromelain and papain protease preparations were also treated with 2-mercaptoethanol to keep the active site cysteines of these two proteases in the reduced (active) state.

Data presented in Table 3 was acquired following a 60 minute incubation of the various proteases with 500 μL IMAC bead-trapped GFP at 37° C. GFP released by protease activity was separated from the beads using nine-inch, glass-bead plugged Pasteur pipettes. Beads were washed with 50 mM Tris, 137 mM NaCl, pH 7.4 buffer and 3.8 mL eluant was collected. A second wash was conducted using 200 mM Tris, 200 mM EDTA, pH 8.0, to release any GFP that had not been released by the protease.

TABLE 3

| Protease | µg GFP Released by Protease | % GFP Released | µg GFP Released by EDTA | Mass Balance (µg) |
|---|---|---|---|---|
| Papain | 109 | 97 | 2.97 | 112 |
| Chymotrypsin | 10.6 | 11 | 85.4 | 96 |
| Trypsin | 4.07 | 4.6 | 85.4 | 89 |
| Bromelain | 109 | 98 | 1.86 | 111 |
| EDTA | 106 | 99 | 1.11 | 107 |
| Untreated | 0 | 0 | 81.7 | 82 |

Eluants of GFP released by cleavage with papain, bromelain, and EDTA, were diluted 20-fold to be on scale with the fluorimeter, i.e., yielding fluorescence units of 400, 400, and 390, respectively. The control, however, was not diluted, indicating that data obtained in this assay is accurate to under 0.05%. Data presented in Table 3 was collected from a fluorimeter with approximately 1% drift. Accordingly, the fluorescence of eluants from papain, bromelain and the untreated control was detected on a more stable machine with the most sensitive setting (i.e., one that generates some noise). Multiplying instrument signal by dilution factor (400-fold dilution), papain yielded an averaged (over four readings) GFP signal of 282,000, whereas bromelain yielded a averaged (over four readings) GFP signal of 281,500. In contrast, the undiluted, untreated control averaged 48 over six readings (i.e., 41, 26, −12, 180, −25, and 75). The resulting experimental-to-control ratio or signal-to-noise ratio of this assay was 5900:1. When compared to ELISA assays, generally having signal-to-noise ratios of approximately 10:1, the instant assay is highly sensitive and can be used to measure small differences in protease activity.

SEQUENCE LISTING

```
<160> NUMBER OF SEQ ID NOS: 25

<210> SEQ ID NO 1
<211> LENGTH: 234
<212> TYPE: PRT
<213> ORGANISM: Artificial Sequence
<220> FEATURE:
<223> OTHER INFORMATION: Synthetic protein

<400> SEQUENCE: 1

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
```

```
                210               215              220
Val Thr Ala Ala Gly Ile Thr His Gly Ala
225                 230
```

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

```
Val Ser Gln Tyr Val Ile Val
1               5
```

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

```
Glu Asn Leu Tyr Phe Gln Gly
1               5
```

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide

<400> SEQUENCE: 4

```
Pro Ser Pro Arg Glu Gly Lys Arg Ser Tyr
1               5                   10
```

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

```
Tyr Val Ala Asp Gly
1               5
```

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

```
Met Phe Gly Gly Ala Lys Lys Arg
1               5
```

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

```
Arg Gly Val Val Asn Ala Ser Ser Arg Leu Ala
1               5                   10
```

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

```
Leu Ile Ala Tyr Leu Lys Lys Ala Thr
1               5
```

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

```
Val Lys Met Asp Ala Glu Phe
1               5
```

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

```
Leu Val Pro Arg Gly Ser
1               5
```

<210> SEQ ID NO 11
<211> LENGTH: 13
<212> TYPE: PRT
<213> ORGANISM: Artificial Sequence
<220> FEATURE:
<223> OTHER INFORMATION: Synthetic peptide

<400> SEQUENCE: 11

```
Asp Arg Val Tyr Ile His Pro Phe His Leu Val Ile His
1               5                   10
```

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

```
Lys Pro Ala Leu Phe Phe Arg Leu
1               5
```

<210> SEQ ID NO 13
<211> LENGTH: 19
<212> TYPE: PRT
<213> ORGANISM: Artificial Sequence
<220> FEATURE:
<223> OTHER INFORMATION: Synthetic peptide

<400> SEQUENCE: 13

-continued

```
Gln Pro Leu Gly Gln Thr Ser Leu Met Lys Arg Pro Pro Gly Phe Ser
1               5                   10                  15

Pro Phe Arg

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Leu Val Leu Ala Ser Ser Ser Phe
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 15

Lys Xaa Tyr Lys
1

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16

Ile Glu Gly Arg
1

<210> SEQ ID NO 17
<211> LENGTH: 245
<212> TYPE: PRT
<213> ORGANISM: Artificial Sequence
<220> FEATURE:
<223> OTHER INFORMATION: Synthetic protein

<400> SEQUENCE: 17

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
        210                 215                 220

Val Thr Ala Ala Gly Ile Thr His Ser Val Pro Ser Gly Cys Gly His
225                 230                 235                 240

His His His His His
                245

<210> SEQ ID NO 18
<211> LENGTH: 258
<212> TYPE: PRT
<213> ORGANISM: Artificial Sequence
<220> FEATURE:
<223> OTHER INFORMATION: Synthetic protein

<400> SEQUENCE: 18

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
        210                 215                 220
```

```
Val Thr Ala Ala Gly Ile Thr His Gly Ala Glu Asn Leu Tyr Phe Gln
225                 230                 235                 240

Gly Ala Glu Asn Leu Tyr Phe Gln Gly Ala Glu Asn Leu Tyr Phe Gln
                245                 250                 255

Gly Cys
```

<210> SEQ ID NO 19
<211> LENGTH: 247
<212> TYPE: PRT
<213> ORGANISM: Artificial Sequence
<220> FEATURE:
<223> OTHER INFORMATION: Synthetic protein

<400> SEQUENCE: 19

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Ala Ile Glu Gly Arg Val Ile
225                 230                 235                 240

Ile Glu Gly Arg Val Ile Cys
                245
```

<210> SEQ ID NO 20
<211> LENGTH: 255
<212> TYPE: PRT
<213> ORGANISM: Artificial Sequence
<220> FEATURE:
<223> OTHER INFORMATION: Synthetic protein

<400> SEQUENCE: 20

```
Met Ala Ser Lys Gly Glu Glu Leu Phe Thr Gly Val Val Pro Ile Leu
1               5                   10                  15
```

-continued

```
Val Glu Leu Asp Gly Asp Val Asn Gly His Lys Phe Ser Val Ser Gly
         20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Phe Ser Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Ala Leu Val Pro Arg Gly Ser
225                 230                 235                 240

Ala Leu Val Pro Arg Gly Ser Ala Leu Val Pro Arg Gly Ser Cys
                245                 250                 255
```

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Ser Val Pro Ser Gly Cys Gly
1               5

<210> SEQ ID NO 22
<211> LENGTH: 741
<212> TYPE: DNA
<213> ORGANISM: Artificial Sequence
<220> FEATURE:
<223> OTHER INFORMATION: Synthetic nucleic acid

<400> SEQUENCE: 22
atggctagca aaggagaaga acttttcact ggagttgtcc caattcttgt tgaattagat      60
ggtgatgtta atgggcacaa attttctgtc agtggagagg gtgaaggtga tgctacatac     120
ggaaagctta cccttaaatt tatttgcact actggaaaac tacctgttcc atggccaaca     180
cttgtcacta ctttctctta tggtgttcaa tgcttttccc gttatccgga tcatatgaaa     240
cggcatgact ttttcaagag tgccatgccc gaaggttatg tacaggaacg cactatatct     300
ttcaaagatg acgggaacta caagacgcgt gctgaagtca agtttgaagg tgataccctt     360
```

```
gttaatcgta tcgagttaaa aggtattgat tttaaagaag atggaaacat tctcggacac    420
aaactcgagt acaactataa ctcacacaat gtatacatca cggcagacaa acaaaagaat    480
ggaatcaaag ctaacttcaa aattcgccac aacattgaag atggatccgt tcaactagca    540
gaccattatc aacaaaatac tccaattggc gatggccctg tccttttacc agacaaccat    600
tacctgtcga cacaatctgc cctttcgaaa gatcccaacg aaaagcgtga ccacatggtc    660
cttcttgagt ttgtaactgc tgctgggatt acacattcgg tacccagcgg ctgcggccac    720
caccaccacc accaccacta a                                              741

<210> SEQ ID NO 23
<211> LENGTH: 774
<212> TYPE: DNA
<213> ORGANISM: Artificial Sequence
<220> FEATURE:
<223> OTHER INFORMATION: Synthetic nucleic acid

<400> SEQUENCE: 23
atggctagca aaggagaaga acttttcact ggagttgtcc caattcttgt tgaattagat     60
ggtgatgtta atgggcacaa attttctgtc agtggagagg gtgaaggtga tgctacatac    120
ggaaagctta cccttaaatt tatttgcact actggaaaac tacctgttcc atggccaaca    180
cttgtcacta ctttctctta tggtgttcaa tgcttttccc gttatccgga tcatatgaaa    240
cggcatgact ttttcaagag tgccatgccc gaaggttatg tacaggaacg cactatatct    300
ttcaaagatg acgggaacta caagacgcgt gctgaagtca agtttgaagg tgataccctt    360
gttaatcgta tcgagttaaa aggtattgat tttaaagaag atggaaacat tctcggacac    420
aaactcgagt acaactataa ctcacacaat gtatacatca cggcagacaa acaaaagaat    480
ggaatcaaag ctaacttcaa aattcgccac aacattgaag atggatccgt tcaactagca    540
gaccattatc aacaaaatac tccaattggc gatggccctg tccttttacc agacaaccat    600
tacctgtcga cacaatctgc cctttcgaaa gatcccaacg aaaagcgtga ccacatggtc    660
cttcttgagt ttgtaactgc tgctgggatt acacatggcg cggaaaacct gtattttcag    720
ggtgccgaaa acctgtattt tcagggtgcc gaaaacctgt attttcaggg ttgc          774

<210> SEQ ID NO 24
<211> LENGTH: 744
<212> TYPE: DNA
<213> ORGANISM: Artificial Sequence
<220> FEATURE:
<223> OTHER INFORMATION: Synthetic nucleic acid

<400> SEQUENCE: 24
atggctagca aaggagaaga acttttcact ggagttgtcc caattcttgt tgaattagat     60
ggtgatgtta atgggcacaa attttctgtc agtggagagg gtgaaggtga tgctacatac    120
ggaaagctta cccttaaatt tatttgcact actggaaaac tacctgttcc atggccaaca    180
cttgtcacta ctttctctta tggtgttcaa tgcttttccc gttatccgga tcatatgaaa    240
cggcatgact ttttcaagag tgccatgccc gaaggttatg tacaggaacg cactatatct    300
ttcaaagatg acgggaacta caagacgcgt gctgaagtca agtttgaagg tgataccctt    360
gttaatcgta tcgagttaaa aggtattgat tttaaagaag atggaaacat tctcggacac    420
aaactcgagt acaactataa ctcacacaat gtatacatca cggcagacaa acaaaagaat    480
ggaatcaaag ctaacttcaa aattcgccac aacattgaag atggatccgt tcaactagca    540
```

-continued

| | |
|---|---|
| gaccattatc aacaaaatac tccaattggc gatggccctg tccttttacc agacaaccat | 600 |
| tacctgtcga cacaatctgc cctttcgaaa gatcccaacg aaaagcgtga ccacatggtc | 660 |
| cttcttgagt ttgtaactgc tgctgggatt acacatggcg cgattgaagg tcgtgtgatc | 720 |
| attgaaggtc gtgtgatctg ctga | 744 |

<210> SEQ ID NO 25
<211> LENGTH: 768
<212> TYPE: DNA
<213> ORGANISM: Artificial Sequence
<220> FEATURE:
<223> OTHER INFORMATION: Synthetic nucleic acid

<400> SEQUENCE: 25

| | |
|---|---|
| atggctagca aaggagaaga acttttcact ggagttgtcc caattcttgt tgaattagat | 60 |
| ggtgatgtta atgggcacaa attttctgtc agtggagagg gtgaaggtga tgctacatac | 120 |
| ggaaagctta cccttaaatt tatttgcact actggaaaac tacctgttcc atggccaaca | 180 |
| cttgtcacta ctttctctta tggtgttcaa tgcttttccc gttatccgga tcatatgaaa | 240 |
| cggcatgact ttttcaagag tgccatgccc gaaggttatg tacaggaacg cactatatct | 300 |
| ttcaaagatg acgggaacta caagacgcgt gctgaagtca agtttgaagg tgatacccct | 360 |
| gttaatcgta tcgagttaaa aggtattgat tttaaagaag atggaaacat tctcggacac | 420 |
| aaactcgagt acaactataa ctcacacaat gtatacatca cggcagacaa acaaaagaat | 480 |
| ggaatcaaag ctaacttcaa aattcgccac aacattgaag atggatccgt tcaactagca | 540 |
| gaccattatc aacaaaatac tccaattggc gatggccctg tccttttacc agacaaccat | 600 |
| tacctgtcga cacaatctgc cctttcgaaa gatcccaacg aaaagcgtga ccacatggtc | 660 |
| cttcttgagt ttgtaactgc tgctgggatt acacatggcg ccctggttcc gcgtggttct | 720 |
| gccctggttc cgcgtggttc tgccctggtt ccgcgtggtt cttgctga | 768 |

What is claimed is:

1. A composition for determining protease activity consisting of a reporter protein fused to at least one protease cleavage sequence, wherein the protease cleavage sequence is directly attached to a solid support via a linker, wherein the linker comprises at least one chemically reactive amino acid residue, and wherein cleavage of the protease cleavage sequence by the protease results in release of the reporter protein.

2. A composition for determining protease activity consisting of a reporter protein fused to at least one protease cleavage sequence, wherein the protease cleavage sequence is directly attached to a solid support via a linker, wherein the linker comprises an affinity tag, a carbohydrate, or an Fc fragment, and wherein cleavage of the protease cleavage sequence by the protease results in release of the reporter protein.

* * * * *